(12) United States Patent
Atanasoska et al.

(10) Patent No.: US 8,728,170 B1
(45) Date of Patent: May 20, 2014

(54) BIOERODIBLE NANO-FIBROUS AND NANO-POROUS CONDUCTIVE COMPOSITES

(75) Inventors: Liliana Atanasoska, Edina, MN (US); James Q. Feng, Maple Grove, MN (US); Jan Weber, Maastricht (NL); James Lee Shippy, III, Roswell, GA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 1731 days.

(21) Appl. No.: 11/694,436

(22) Filed: Mar. 30, 2007

Related U.S. Application Data

(60) Provisional application No. 60/877,484, filed on Dec. 28, 2006.

(51) Int. Cl.
*A61F 2/02* (2006.01)
*A61F 2/00* (2006.01)

(52) U.S. Cl.
USPC .............. 623/23.72; 623/15.12; 623/23.75; 623/23.76; 424/423; 424/426

(58) Field of Classification Search
USPC .......... 623/13.11, 13.12, 13.17, 13.18–15.12, 623/23.75, 1.38–1.44, 1.49–1.51, 1.53, 623/1.54; 607/2; 424/422, 423, 426
See application file for complete search history.

(56) References Cited

U.S. PATENT DOCUMENTS

| | | | |
|---|---|---|---|
| 5,385,776 A | 1/1995 | Maxfield et al. | |
| 5,587,507 A | 12/1996 | Kohn et al. | |
| 5,733,925 A | 3/1998 | Kunz et al. | |
| 6,095,148 A * | 8/2000 | Shastri et al. | 128/898 |
| 6,251,980 B1 | 6/2001 | Lan et al. | |
| 6,287,332 B1 | 9/2001 | Bolz et al. | |
| 6,475,477 B1 | 11/2002 | Kohn et al. | |
| 6,899,731 B2 | 5/2005 | Li et al. | |
| 6,918,869 B2 | 7/2005 | Shaw et al. | |
| 6,923,996 B2 | 8/2005 | Epstein et al. | |
| 2002/0004060 A1 | 1/2002 | Heublein et al. | |
| 2002/0034796 A1* | 3/2002 | Shastri et al. | 435/173.1 |
| 2004/0034435 A1* | 2/2004 | Atala | 623/23.65 |
| 2004/0058887 A1 | 3/2004 | Bowlin et al. | |
| 2005/0112349 A1 | 5/2005 | Laurencin et al. | |
| 2006/0051401 A1* | 3/2006 | Manohar et al. | 424/443 |
| 2006/0085063 A1* | 4/2006 | Shastri et al. | 623/1.41 |

FOREIGN PATENT DOCUMENTS

WO WO93/14118 7/1993

OTHER PUBLICATIONS

Li et al., "Electrospinning polyaniline-contained gelatin nanofibers for tissue engineering applications," Biomaterials, 27(13):2705-2715, 2006.
Li et al., "[Research progresses on electroactive and electrically conductive polymers for tissue engineering scaffolds]," Zhongguo Yixue Kexueyuan Xuebao—ACTA Academiae Medicinae Sinicae, Beijing, CN, 28(6):845-848, 2006.
Schmidt et al., "Stimulation of neurite outgrowth using an electrically conducting polymer," Proc. Natl. Acad. Sci. U.S.A., 94(17):8948-8953, 1997.

(Continued)

*Primary Examiner* — David Isabella
*Assistant Examiner* — Yashita Sharma
(74) *Attorney, Agent, or Firm* — Fish & Richardson P.C.

(57) ABSTRACT

A bioerodible conductive tissue scaffold that can provide, e.g., improved tissue growth.

16 Claims, 3 Drawing Sheets

(56) References Cited

OTHER PUBLICATIONS

Wang et al., "A biodegradable electrical bioconductor made of polypyrrole nanoparticle/poly(D,L-lactide) composite: A preliminary in vitro biostability study," *J. Biomed. Mater. Res.*, 66(4):738-746, 2003.
Berkland et al., "Controlling surface nano-structure using flow-limited field-injection electrostatic spraying (FFESS) of poly(D,L-lactide-co-glycolide)," *Biomaterials*, vol. 25:5649-5658 (2004).
Carpi et al., "Colours from electroactive polymers: Electrochromic, electroluminescent and laser devices based on organic materials," *Optics & Laser Technology*, vol. 38:292-305 (2006).
Chandra et al., "Biodegradable polymers," *Progress in Polymer Science* 23:1273-1335 (1998).
Chen et al., "Electrochemical characteristics of bilayer film of polyaniline composite positive with polymer electrolyte binder/polymer electrolyte for Li-ion batteries," *Journal of Power Sources* 102:112-117 (2001).
Cheng et al., Drexel University, Ph.D. Thesis, "Chapter 6: Bioapplicable conducting Polymers based on a Biological Template Guided Synthesis," 149-178 (2002).
Choi et al., "Poly(3,4-ethylenedioxythiophene) nanoparticles prepared in aqueous DBSA solutions," *Sythetic Metals* 141:293-299 (2004).
U.S. Appl. No. 60/845,136, filed Sep. 15, 2006, Weber et al.
U.S. Appl. No. 60/844,898, filed Sep. 15, 2006, Atanasoska et al.
U.S. Appl. No. 10/849,742, filed May 20, 2004, Chen et al.
Chronakis et al., "Conductive polypyrrole nanofibers via electrospinning: Electrical and morphological properties," *Polymer* 47:1597-1603 (2006).
Cooper et al., "Fiber-based tissue-engineered scaffold for ligament replacement: design considerations and in vitro evaluation," *Biomaterials* 26:1523-1532 (2005).
George et al., "Fabrication and biocompatibility of polypyrrole implants suitable for neural prosthetics," *Biomaterials* 26:3511-3519 (2005).
Hopkins et al., "Inerfacial synthesis of electrically conducting polyaniline nanofiber composites," *Thin Solid Films* 469-470:304-308 (2004).
Ikegame et al., "Template Synthesis of Polypyrrole Nanofibers Insulated within One-Dimensional Silicate Channels: Hexagonal versus Lamellar for Recombination of Polarons into Bipolarons," *Angew. Chem. Int. Ed. Engl.* 42:2154-2157 (2003).
Ivaska, "Conducting polymers and their applications," University of Alicante, Department of Chemistry, Alicante, Spain (2006) (39 pages).
Jagur-Grodzinski, "Biomedical application of functional polymers," *Reactive and Functional Polymers* 39:99-138 (1999).
Jang et al., "Observation of photoluminescence in polypyrrole micelles," *Synthetic Metals* 150:127-131 (2005).
Khor et al., "Interaction of chitosan with polypyrrole in the formation of hybrid biomaterials," *Carbohydrate Polymers* 26:183-187 (1995).
Lakard et al., "Culture of neural cells on polymers coated surfaces for biosensor applications," *Biosensors and Bioelectronics* 20:1946-1954 (2005).
LaVan et al., "Simple, Three-Dimensional Microfabrication of Electrodeposited Structures," *Angew. Chem. Int. Ed.* 42:1262-1265 (2003).
Lee et al., "A novel conducting soluble polypyrrole composite with a polymeric co-dopant," *Synthetic Metals* 114:347-353 (2000).
Lee et al., "Electrochemical characteristics of PAN ionomer based polymer electrolytes," *Electrochimica Acta* 45:1301-1306 (2000).
Li et al., "Improved surface properties of polyaniline films by blending with Pluronic polymers without the modification of the other characteristics," *Journal of Colloid and Interface Science* 264:362-369 (2003).
Luo et al., "Amperometric ammonium ion sensor based on polyaniline-poly(styrene sulfonate-*co*-maleic acid) composite conducting polymeric electrode," *Sensors and Actuators B: Chemical* 115: 102-108 (2006).
MacDiarmid, ""Synthetic Metals": A Novel Role for Organic Polymers (Nobel Lecture)," *Angew. Chem. Int. Ed. Engl.* 40:2581-2590 (2001).
Min et al., "Chitin and chitosan nanofibers: electrospinning of chitin and deacetylation of chitin nanofibers," *Polymer* 45:7137-7142 (2004).
Moore et al., "Multiple-channel scaffolds to promote spinal cord axon regeneration," *Biomaterials* 27:419-429 (2006).
Nilsson et al., "Mathematical modeling of physicochemical reactions and transport processes occurring around a platinum cathode during the electrochemical treatment of tumors," *Bioelectrochemistry* 53:213-224 (2001).
Ramakrishnan, "Conducting Polymers—From a Laboratory Curiosity to the Market Place," *Resonance* 2:48-58 (1997).
Ramanaviciene et al., "AFM study of conducting polymer polypyrrole nanoparticles formed by redox enzyme—glucose oxidase—initiated polymerisation," *Colloids and Surfaces B: Biointerfaces* 48:159-166 (2006).
Riess, "Polymeric mixed ionic electronic conductors," *Solid State Ionics* 136-137:1119-1130 (2000).
Schmidt et al., "Neural Tissue Engineering: Strategies for Repair and Regeneration," *Annual Review of Biomedical Engineering* 5:293-347 (2003).
Shi et al., "A novel electrically conductive and biodegradable composite made of polypyrrole nanoparticles and polylactide," *Biomaterials* 25:2477-2488 (2004).
Shin et al., "Synthesis of conducting polyanilline in semi-IPN based on chitosan," *Synthetic Metals* 154:213-216 (2005).
Siepmann et al., "Mathematical modeling of bioerodible, polymeric drug delivery systems," *Advanced Drug Delivery Reviews* 48:229-247 (2001).
Song et al., "Review of gel-type polymer electrolytes for lithium-ion batteries," *Journal of Power Sources* 77:183-197 (1999).
Song et al., "Micropattems of positive guidance cues anchored to polypyrrole doped with polyglutmic acid: A new platform for characterizing neurite extension in complex environments," *Biomaterials* 27:473-484 (2006).
University of Central Florida, http://reach.ucf.edu/~OncEduc1, Jan. 17, 2008.
Wan et al., "Poly (3,4-ethylenedioxythiophene) nanoparticles prepared in aqueous DBSA solutions," *Synthetic Materials* 141:293-299 (2004).
Wan et al., "Preparation and characterization of porous conducting poly(DL-lactide) composite membranes," *Journal of Membrane Science* 246:193-201 (2005).
Wanekaya et al., "Nanowire-Based Electrochemical Biosensors," *Electroanalysis* 18:533-550 (2006).
Wang et al., "In vivo evaluation of a novel electrically conductive polypyrrole/poly($_{D,L}$-lactide) composite and polypyrrole-coated poly ($_{D,L}$-lactide-*co*-glycolide) membranes," *Journal of Biomedical Materials Research Part A*, vol. 70A:28-38 (2004).
Zelikin et al., "Erodible Conducting Polymers for Potential Biomedical Applications," *Angew. Chem. Int. Ed. Engl.* 41:141-144 (2002).
Zhang, "Fabrication of novel biomaterials through molecular self-assembly," *Nature Biotechnology* 21:1171-1178 (2003).
Zhang et al., "Designer self-assembling peptide nanofiber scaffolds for 3D tissue cell cultures," *Seminars in Cancer Biology* 15:413-420 (2005).
Zong et al., "Electrospun fine-textured scaffolds for heart tissue constructs," *Biomaterials* 26:5330-5338 (2005).
Conducting Polymers www.ch.ic.ac.uk/local/organic/tutorials/steinke/4yrPolyConduct2003.pdf.

\* cited by examiner

BIOERODIBLE NANO-FIBROUS AND NANO-POROUS CONDUCTIVE COMPOSITES

CROSS-REFERENCE TO RELATED APPLICATION

This application claims the benefit of the filing date of U.S. Provisional Patent Application Ser. No. 60/877,484, filed on Dec. 28, 2006, the entire contents of which are hereby incorporated by reference.

TECHNICAL FIELD

This application relates to medical devices including bioerodible composites, and methods of making the devices.

BACKGROUND

For a variety of medical conditions, treatment can sometimes involve a regrowth or a replacement of a body tissue, such as bone, muscle, nerves, blood vessels, connective tissue, and skin. A medical device such as a tissue scaffold is sometimes used to aid tissue regrowth or replacement. The tissue scaffold can be a structure capable of supporting and assisting a variety of processes in tissue growth, such as cell attachment, proliferation, differentiation, and migration. In some cases, the tissue scaffold can assist in directing or orienting cell growth. Cells of a desired type of body tissue can be isolated, seeded and cultured on the tissue scaffold, and implanted or grafted into a patient. Sometimes, the seeded or unseeded tissue scaffold can be directly implanted into a body to aid the body in growing the desired tissue.

SUMMARY

The invention relates to medical devices, such as tissue scaffolds, and methods of making the devices. In embodiments, the devices can be configured to be electrically or ionically conducting and can erode in a controlled and predetermined manner in the body.

In one aspect, the invention features a tissue scaffold including a plurality of polymeric filaments including a conducting polymer, the scaffold being at least partially soluble.

In another aspect, the invention features a method of making a medical device, including flow-limited field-injection electrostatic spraying a polymer solution to form a polymer member on a substrate, the polymer member being at least partially bioerodible and including a conducting polymer.

Embodiments of aspects of the invention may include one or more of the following features.

At least some of the filaments of the tissue scaffold can have a diameter of about 5-500 nm. In some embodiments, substantially all of the filaments (e.g., >95%, >90%) can have a diameter of about 5-500 nm. The polymer member can include filaments with a diameter from about 5 nm to about 500 nm. The filaments can have a substantially uniform diameter along a length. The filaments have a length of from about 10 micrometers to about 10 centimeters. The filaments can have a lengthtodiameter aspect ratio of from about 100:1 to about 10,000:1. The filaments can define pores; the pores can have a diameter from about 5 micrometers to about 25 micrometers.

The conducting polymer is bioerodible or non-erodible. The conducting polymer can have a conductivity of from about 0.1 Scm$^{-1}$ to about 50 Scm$^{-1}$. The conducting polymer can include a polymer such as polypyrrole, polythiophene, polyanilline, substituted polypyrrole, substituted polythiophene, substituted polyaniline, and/or combinations thereof. The substituted polypyrrole, substituted polythiophene, and substituted polyaniline can include a side chain including an ionizable and hydrolysable moiety. In some embodiments, the conducting polymer includes an anionic dopant. The anionic dopant can include chloride, sulfate, perchlorate, dodecylbenzene sulfonic acid, poly(acrylamide-methyl-propane sulfonic acid), and/or combinations thereof.

The filaments can include a combination of polymers, including a conducting and a non-conducting polymer. The non-conducting polymer is erodible or non-erodible. The non-conducting polymer can include poly(D,L-lactide), poly(D,L-lactide-co-glycolide), polyanhydride, and/or combinations thereof.

The tissue scaffold can include a first filament having a first conducting polymer and a second filament having a second conducting polymer. The second conducting polymer can include polypyrrole, polythiophene, polyaniline, substituted polypyrrole, substituted polythiophene, substituted polyaniline, and/or combinations thereof. The tissue scaffold can include a first filament including a conducting polymer and a second filament without a conducting polymer. The second filament can include poly(D,L-lactide), poly(D,L-lactide-co-glycolide), polyanhydride, and/or combinations thereof. The second filament can include a composite. In some embodiments, the second filament is different from the first filament.

The tissue scaffold can include a vascular tissue scaffold, a cardiac tissue scaffold, a neural tissue scaffold, a bioelectric circuit, a neuron-vascular network, and/or a neural implant.

The method can further include flow-limited field-injection electrostatic spraying nanoparticles. The nanoparticles can have a diameter of from about 5 nm to 1000 nm. In some embodiments, the substrate is a rotating drum or a rotating disk. In some embodiments, flow-limited field-injection electrostatic spraying the polymer solution can include spraying a plurality of polymer solutions.

Embodiments may have one or more of the following advantages. The tissue scaffold can help support tissue growth. The tissue scaffold can be bioerodible. For example, the tissue scaffold can bioerode completely after a period of cell growth. The tissue scaffold can include bioerodible electrically conductive polymers in the form of nanofilaments or nanoparticles, which can be electrically stimulated and/or can affect (e.g., enhance, inhibit, and/or direct) the growth and behavior of cells in processes such as cellular attachment, proliferation, differentiation, and/or migration. The tissue scaffold can include bioerodible polymer nanofilaments or nanoparticles, which can be modified to relatively easily tailor the bioerosion rate and biocompatibility of the tissue scaffold. The tissue scaffold can be adapted for a variety of tissues such as epithelial, connective, muscle, and nerve cells, which can include skin, spinal cord, brain, bone, cartilage, valve, muscle, blood vessel, and retinal tissues. The tissue scaffold can be made by flow-limited field-injection electrostatic spraying (FFESS) nanofilaments and/or nanoparticles of bioerodible conducting and/or non-conducting polymers, with good control over the size (e.g., width and/or diameter). FFESS can inject charge into a polymer solution and can be relatively independent of the polymers and solvents.

The details of one or more embodiments of the invention are set forth in the accompanying drawings and the description below. Other aspects, features, and advantages of the invention will be apparent from the description and drawings, and from the claims.

DETAILED DESCRIPTION

Figure 1A:
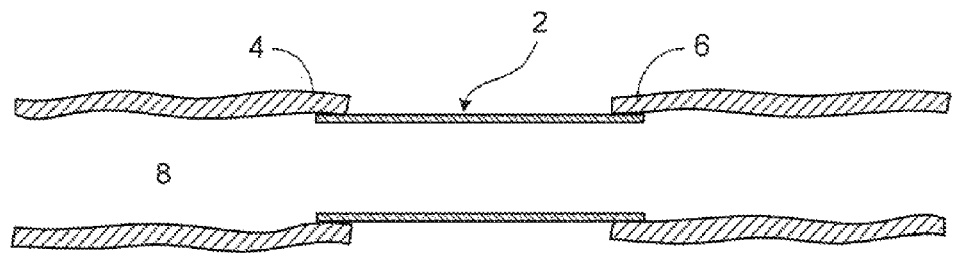
FIG. 1A-1C are sequential cross-sectional views of a tissue scaffold in place in a vessel over time.
Figure 1B:
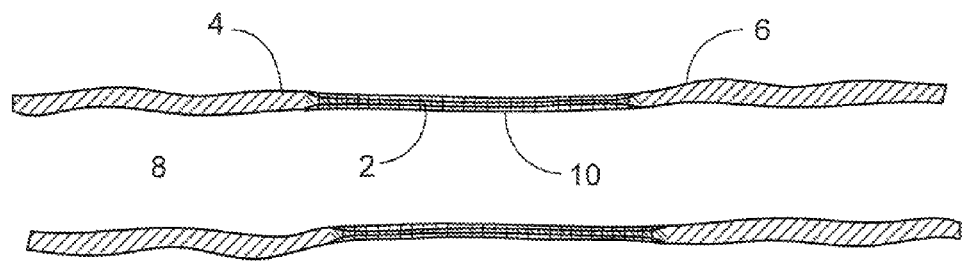
Figure 1C:
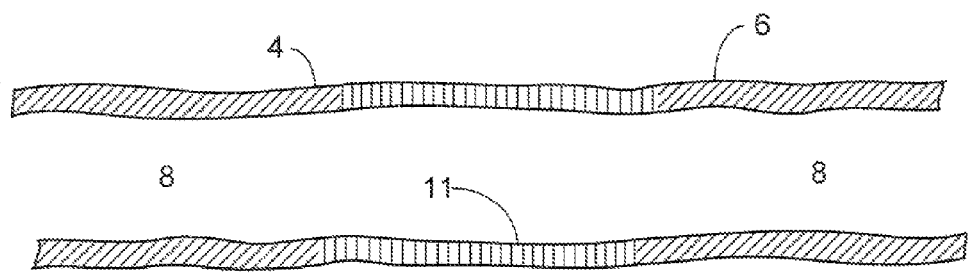

Referring to FIG. 1A, a tissue scaffold 2 is illustrated in place in the body. The scaffold 2 is a generally tubular element that has been implanted between two ends 4, 6, of a vessel 8, such as a blood vessel. The scaffold 2 can be implanted surgically, for example after excising a section of the vessel which is occluded or weakened. The scaffold can also be implanted using minimally invasive techniques, such by delivery over a catheter, such as a balloon catheter. Referring particularly to FIG. 1B, over time, tissue growth 10 is encouraged along and encapsulates the scaffold 2. Referring to FIG. 1C, tissue growth continues and the scaffold partially or completely bioerodes, leaving the vessel substantially patent with a new growth region 11. A tissue scaffold can be adapted for a variety of tissues such as epithelial, connective, muscle, and nerve cells, which can include spinal cord, brain, valve, muscle, blood vessel, skin, bone, cartilage, and retinal tissues.

Figure 2A:
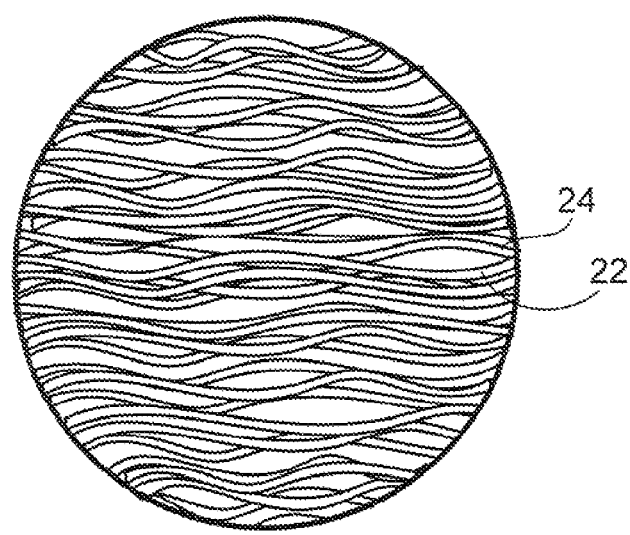
FIG. 2A is an enlarged view of an embodiment of a medical device.
Figure 2B:
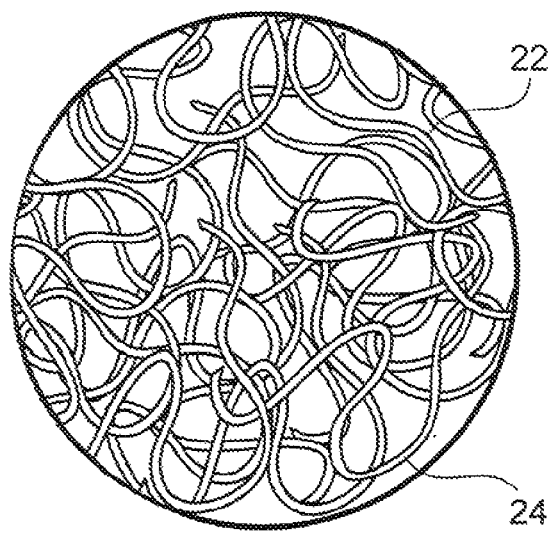
FIG. 2B is an enlarged view of an embodiment of a medical device.

Referring as well to FIGS. 2A and 2B, in embodiments, the scaffold 2 is formed of fine polymeric fibers 22, 24, with diameters in the nanometer range, that have electrically conductive and biodegradable properties. Referring particularly to FIG. 2A, in embodiments, the fibers 22, 24 can be arranged to extend in a generally common direction. Referring particularly to FIG. 2B, the fibers can, alternatively, extend in various directions. The fibers form a porous structure that encourages and supports tissue growth. In embodiments, the fibers 22, 24 can be composed of the same polymer, e.g. an electrically conductive polymer, or combination of polymers. Alternatively, the fibers can be made of different polymer compositions. For example, fiber 22 can be formed of conductive polymer(s) and fiber 24 can be formed of nonconductive polymer(s). One or both of the fibers can include biodegradable polymers, such that one of the fibers is at least partially degradable or both of the fibers are at least partially degradable.

Figure 3:
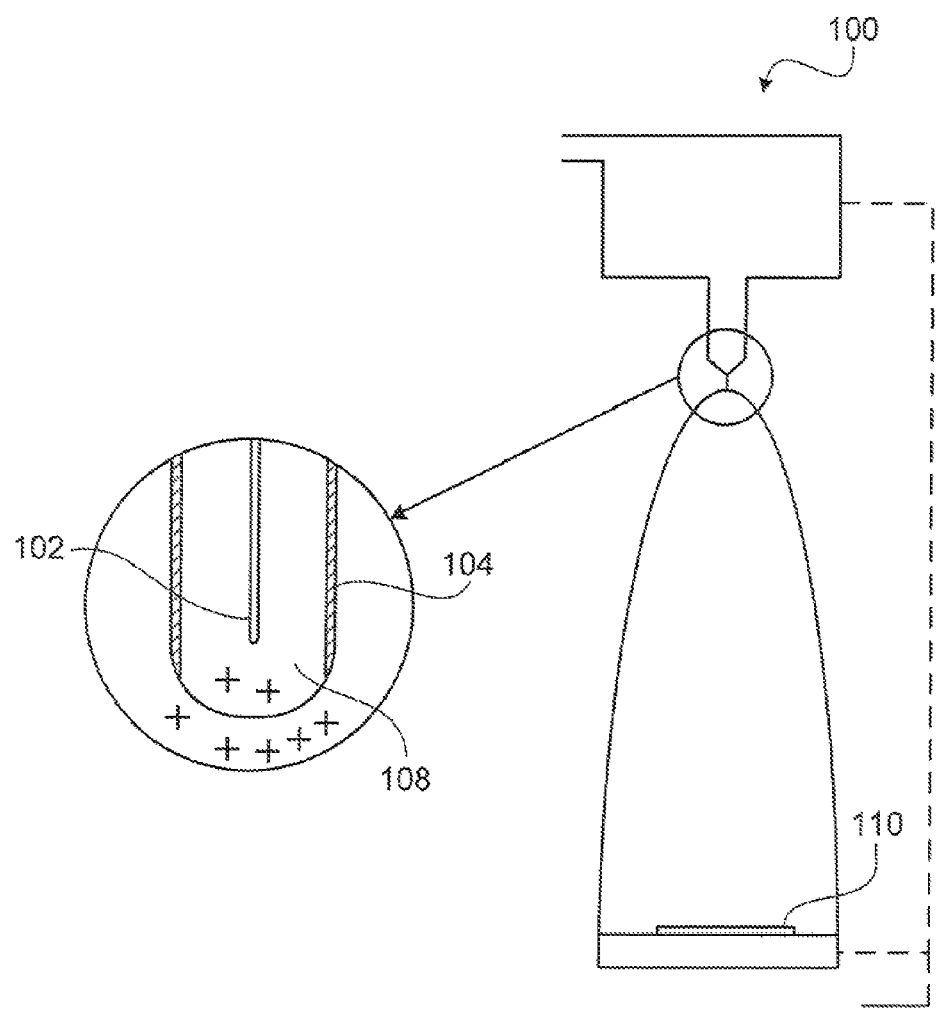
FIG. 3 is a scheme illustrating a method of making a medical device.

Referring as well to FIG. 3, the scaffolds are formed by flow-limited field-injection electrostatic spraying (FFESS) system 100. In FFESS, a polymer/solvent solution is directed through a charged sharpened needle 102, e.g. tungsten, held in a capillary 104 to inject charge onto the solution 108 as it is directed in the form of a spray toward a grounded collection target 110. DC voltage is applied between the nozzle and the collection substrate. As the spray is drawn toward the collection substrate, the solvent evaporates to generate polymer fibers or particles. The FFESS system is adapted for selected polymer(s) and solvent(s), including noncharged solvents and polymers because it injects charge into the solution when needed during spraying. The tungsten needle 102 can be negatively or positively charged, and can inject either negative or positive charge into the polymer/solvent solution. In some embodiments, a negatively charged tungsten needle generates fibers by field emission, and/or a positively charged tungsten needle generates fibers by field ionization. The system allows control of the composition, fiber size and arrangement, porosity, and conductivity. For example, the fibers can have a diameter of about 500 nm or less, e.g. about 10 to 100 nm. In some embodiments, FFESS allows for a high degree of control over shape and flow regimes, and/or can enhance jet stability and uniformity of the sprayed polymer solution. FFESS is also further discussed, for example, in Berkland et al., Biomaterials, 25 (2004), 5649-5658.

In some embodiments, a filament includes one or more conducting polymers. A conducting polymer is a compound capable of conducting (e.g., transporting) an electric charge and/or ions and having one, preferably two or more, repeating covalently linked monomers. For example, a polymer can include greater than about 10 covalently linked monomers (e.g., greater than 100 monomers, greater than 1000 monomers, greater than 10,000 monomers, greater than 100,000 monomers). The polymer can be crosslinked, branched, linear, amorphous, and/or crystalline. Without being bound by theory, it is believed that the conducting polymer can be electrically stimulated and is capable of affecting (e.g., enhancing, inhibiting, and/or directing) the growth and behavior of cells in cellular attachment, proliferation, differentiation, and migration processes. In some embodiments, a conductive polymer is an electrically conducting polymer and/or solid polymer electrolyte. In some embodiments, a non-conductive polymer can be loaded with metals or carbon to become electrically or ionically conductive. Examples of conducting polymers include polypyrroles, polythiophenes, polyanilines, poly(para-phenylene)s, poly(phenylene vinylene)s, poly(ethenylene vinylene)s, poly(phenylene sulfide)s, poly(phenylene ethynylene)s, poly(acetylene)s, poly (pyridine)s, poly(diphenylamine)s, polyindoles, and/or poly (acrylonitrile-co-lithium methacrylate). Examples of conducting polymers are described, for example, in Lee et al., Electrochimica Acta, 45 (2000), 1301-1306; Wanekaya et al., Electroanalysis, 18 (2006), 533-550; Ramakrishnan S., Resonance, 2 (1997), 48-58; MacDiarmid, A. G., Angew. Chem. Int. Ed., 40 (2001), 2581-2590; Carpi et al., Optics & Laser Technology, 38 (2006), 292-305; and Riess I, Solid State Ionics, 136-137 (2000), 1119-1130. Synthesis of a conducting polymer such as polypyrrole is described, for example, in Ikegame et al., Angew. Chem. Int. Ed., 42 (2003), 2154-2157; and LaVan et al., Angew. Chem. Int. Ed., 42 (2003), 1262-1265. Examples of ionically conductive polymers include poly(ethylene oxide), poly(acrylonitrile), poly(methyl methacrylate), polyvinyl chloride, and poly(vinylidene fluoride). Ionically conductive polymers are described, for example, in Song et al., Journal of Power Sources, 77 (1999), 183-197. The conducting polymer can include an anionic dopant, which can include organic ions, inorganic ions, monomeric and/or polymeric ions. The anionic dopant can increase the solubility of a conductive polymer. Examples of anionic dopants include chloride, sulfate, perchlorate, dodecylbenzene sulfonic acid, poly(styrenesulfonate-co-maleic acid), poly(glutamic acid), and/or poly(acrylamido-methyl-propane sulfonic acid). A dopant is described, for example, in Lee et al., Synthetic Metals, 114 (2000), 347-353; Luo et al., Sensors and Actuators, 115 (2006) 102-108; and George et al., Biomaterials, 26 (2005), 3511-3519. The conducting polymer can be part of a conductive blend. Examples of conductive blends are described, for example, in Chen et al., Journal of Power Sources, 102 (2001), 112-117. In some embodiments, the conducting polymer (e.g., polypyrrole) includes an oxidant, such as ammonium persulfate, iron trichloride, and/or $H_2O_2$ and transition metal salts (e.g., $Fe^{3+}$, $Ce^{4+}$, $Cu^{2+}$, $Cr^{6+}$, $Mn^{7+}$ complexes). In embodiments, the conducting polymer can have a conductivity from about 0.1 $Scm^{-1}$ to about $10^5$ $Scm^{-1}$. The polymer conductivity can be greater than or equal to about 0.1 $Scm^{-1}$, about 10 $Scm^{-1}$, about 100 Scm$^{-1}$, about 1000 Scm$^{-1}$, or about 10$^4$ Scm$^{-1}$; and/or less than or equal to about 10$^5$ Scm$^{-1}$, about 10$^4$ Scm$^{-1}$, about 1000 Scm$^{-1}$, about 100 Scm$^{-1}$, about 10 Scm$^{-1}$, or about 1 Scm$^{-1}$.

In embodiments, the filament can be bioerodible, for example, by including one or more bioerodible conducting polymers. A bioerodible conducting polymer can include polypyrroles, polythiophenes, polyanilines, poly(para-phenylene)s, poly(phenylene vinylene)s, poly(thenylene-vinylene)s, poly(phenylene sulfide)s, poly(phenylene ethynylene)s, poly(pyridine)s, poly(diphenylamide)s, and/or polyindoles substituted with ionizable and/or hydrolyzable moieties, such as esters or carboxylic acids. Erodible conducting polymers are described, for example, in Zelikin et al., Angew. Chem. Int. Ed., 41 (2002), 141-144. Examples of bioerodible conducting polymers are shown in Scheme 1.

Scheme 1

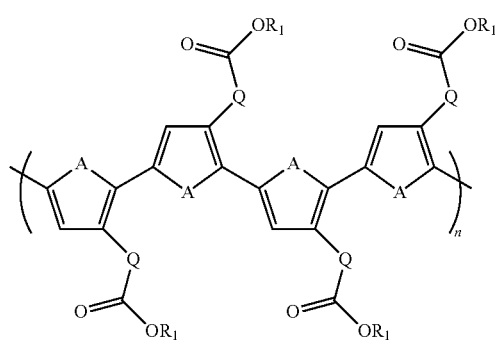

A = NH, or S
Q = a bond, C$_1$—C$_6$ alkyl, C$_1$—C$_5$ alkoxy, C$_1$—C$_5$ alkyl amino, or C$_1$—C$_5$ thioalkyl
R$_1$ = H, or C$_1$—C$_6$ alkyl An example of a bioerodible conducting polymer is polypyrrole (A=NH) substituted with n-propionic methyl ester (e.g., Q=C$_3$, R$_1$=CH$_3$) or n-propionic acid (e.g., Q=C$_3$, R$_1$=H). In some embodiments, a bioerodible conducting polymer is a copolymer (e.g., a random copolymer, an alternating copolymer, a block copolymer) including two or more types of monomers (e.g., three types of monomers, four types of monomers, five types of monomers). The properties of a copolymer (e.g., conductivity, bioerodibility, solubility) can be tailored by changing the mole percent of one or more types of monomers for polymerization and/or by changing the side chains of one or more monomers. As an example, a copolymer can include a combination of n-propionic methyl ester-substituted pyrrole and unsubstituted pyrrole monomers. As another example, a copolymer can include a combination of n-propionic acid-substituted pyrrole and unsubstituted pyrrole monomers. In some embodiments, a bioerodible conducting polymer is a conducting polymer that is grafted onto a bioerodible molecule. Examples of grafted bioerodible conducting polymers are described, e.g., in Cheng et al., Drexel University, Ph.D. Thesis, 2002, Chapter 6, 149-178. In some embodiments, a conducting polymer can be blended with bioerodible biocompatible polymers, which can become conductive by doping the blend with ionic molecules. Examples of biocompatible polymers are described, for example, in Jagur-Grodzinski, Reactive & Functional Polymers, 39 (1999), 99-138; Li et al., Journal of Colloid and Interface Science, 264 (2003), 362-369. In some embodiments, a blend of different conductive polymers can be used in a fiber. In some embodiments, different conductive polymers can be used in different fibers.

In embodiments, the fiber is formed of a composite or a blend of a conducting polymer and one or more bioerodible polymers or other components, which may be conducting or non-conducting. Examples of conducting polymers are as previously described. A bioerodible second polymer can be, for example, poly(D,L-lactide), poly(D,L-lactide-co-glycolide), polyanhydride, poly(cyanoacrylate), poly(ketal), poly(ortho ester), poly(acetal), poly(α-hydroxy-ester), poly(ε-caprolactone), poly(phosphazene), poly(β-hydroxy ester), poly(imino-carbonate), polypeptide, poly(carbonate), and/or polyphosphate ester). Bioerodible polymers are described in, e.g., Min et al., Polymer, 45 (2004), 7137-7142; Chandra et al., Prog. Polym. Sci., 23 (1998), 1273-1335; and Siepmann et al., Advanced Drug Delivery Reviews, 48 (2001), 229-247.

An example of a composite is a multiphase mixture of two polymers, such as polypyrrole and PLA, in which a combination of different materials (e.g., polymers, metals, ceramics, and/or glasses) remains mixed together, and the different materials retain their identities and properties. The composite filament can have characteristics that cannot be obtained by any of the individual components. Composites are described, for example, in Shi et al., Biomaterials, 25 (2004), 2477-2488; and Wan et al., Journal of Membrane Science, 246 (2005), 193-201. Conductive polymer composites are described, for example, in Luo et al., Sensor and Actuators B, 115 (2006), 102-108; Wang et al., J. Biomed. Mater. Res., 70A (2004), 28-38; and Hopkins et al., Thin Solid Films, 469-470 (2004), 304-308.

An example of a blend is a macroscopically homogeneous mixture of two or more polymer chains, such as a polypyrrole and a substituted polypyrrole, in intimate combination but not bonded to each other. As an example, a blend can include chitosan with polyaniline and/or polypyrrole. As an example, a blend can include polyanilline with collagen, and/or polypyrrole with polyglutamic acid. As another example, a blend can include polyaniline with polystyrene and/or polyethylene oxide. Blends are described in, e.g., Cheng, S., Nanostructured, Electroactive, and Bioapplicable Materials, Ph.D. Thesis (2002), Drexel University, 149-178; Shin et al., Synthetic Metals, 154 (2005), 213-216; Khor et al., Carbohydrate Polymers, 26 (1995), 183-187; and Song et al., Biomaterials, 27 (2006), 473-484. The blend or composite can include more than two components, e.g. three to five components or more.

A filament including a composite or a blend can have properties that can be tailored by selecting suitable individual components and their amounts. For example, a bioerosion rate of filament can be varied by changing the weight percent and/or the molecular weight of a particular polymeric component. Depending on the composition of the individual components, a filament can be conducting or non-conducting. In some embodiments, a filament includes the bioerodible second polymer at a concentration from about five weight percent to about 100 weight percent. The bioerodible second polymer concentration can be greater than or equal to about five weight percent, about 10 weight percent, about 15 weight percent, about 20 weight percent, about 25 weight percent, about 30 weight percent, about 35 weight percent, about 40 weight percent, about 45 weight percent, about 50 weight percent, about 55 weight percent, about 60 weight percent, about 65 weight percent, about 70 weight percent, about 75 weight percent, about 80 weight percent, about 85 weight percent, about 90 weight percent, or about 95 weight percent; and/or less than or equal to about 100 weight percent, about 95 weight percent, about 90 weight percent, about 85 weight percent, about 80 weight percent, about 75 weight percent, about 70 weight percent, about 65 weight percent, about 60 weight percent, about 55 weight percent, about 50 weight percent, about 45 weight percent, about 40 weight percent, about 35 weight percent, about 30 weight percent, about 25 weight percent, about 20 weight percent, about 15 weight percent, or about 10 weight percent. A filament that includes a relatively high amount of bioerodible second polymer can erode at a faster rate and can enhance integration of a newly generated tissue within a subject.

In some embodiments, filament 24 includes a bioerodible conducting polymer. The conducting polymer can be the same polymer as in filament 22, or a different bioerodible conducting polymer (e.g., a third polymer). Filament 24 can contain the bioerodible conducting polymer at a concentration from about five weight percent to about 100 weight percent. The bioerodible conducting polymer concentration can be greater than or equal to about five weight percent, about 10 weight percent, about 15 weight percent, about 20 weight percent, about 25 weight percent, about 30 weight percent, about 35 weight percent, about 40 weight percent, about 45 weight percent, about 50 weight percent, about 55 weight percent, about 60 weight percent, about 65 weight percent, about 70 weight percent, about 75 weight percent, about 80 weight percent, about 85 weight percent, about 90 weight percent, or about 95 weight percent; and/or less than or equal to about 100 weight percent, about 95 weight percent, about 90 weight percent, about 85 weight percent, about 80 weight percent, about 75 weight percent, about 70 weight percent, about 65 weight percent, about 60 weight percent, about 55 weight percent, about 50 weight percent, about 45 weight percent, about 40 weight percent, about 35 weight percent, about 30 weight percent, about 25 weight percent, about 20 weight percent, about 15 weight percent, or about 10 weight percent. A filament that includes a relatively high amount of a bioerodible conductive polymer can be relatively conductive, can be electrically stimulated during cell growth, and/or can enhance cell growth.

In embodiments, the fibers 22, 24 can be composed of the same blend or composite or different blends or composites. For example, the fibers 22, 24 can have different conducting polymer(s) (amount or chemical composition), while the other components, e.g. bioerodible polymers or other materials are the same. Alternatively, the fibers can have the same can have more than two conducting polymer(s) while the other components differ, e.g. bioerodible polymers or other materials. The scaffold can have more than two types of fibers, e.g. three or more types of fibers.

In some embodiments, the tissue scaffold exhibits a select degree and/or rate of degradability. For example, the scaffold may be completely erodible by use of filaments formed substantially of erodible polymers. Alternatively, the scaffold can be partially erodible. For example, one of the filaments may be substantially erodible, while the other filament is substantially nonerodible. For example, the nonerodible filament can be formed of nonerodible conductive or nonconductive polymers and the erodible filament formed of erodible conductive or nonconductive polymers. In some embodiments, only portions of the tissue scaffold exhibit bioerodibility. For example, an interior portion may be non-bioerodible, while an exterior portion is bioerodible.

In some embodiments, the bioerodible tissue scaffold exhibits substantial mass reduction after a period of time for which a function of the material, such as support of the newly formed tissue and/or delivery of a therapeutic agent in the immediate vicinity of the scaffold, is no longer needed or desirable. In some embodiments, over the period that the scaffold supports cell growth, the tissue scaffold can undergo at least one erosion process such as dissolution, absorption, erosion, corrosion, resorption, and/or chemical transformation. In some embodiments, the tissue scaffold includes one or more bioerodible polymers that dissociate, depolymerize, hydrolyze, or otherwise reduce in molecular weight from the starting molecular weight of the polymers, such that a resulting compound is soluble in an aqueous solution or can be suspended in a body fluid and transported away from an implantation site without obstructing the flow of the body fluid. Filaments 22 and/or 24 can exhibit a mass reduction (e.g., through bioerosion) of at least about 10%, at least about 20%, at least about 25%, at least about 30%, at least about 50%, at least about 75%, or at least about 90%, after a period of tissue culture. The period of implantation over which the mass reduction through bioerosion takes place can be chosen to be about one day or more, about 14 days or more, about 30 days or more, about 60 days or more, about 90 days or more, about 180 days or more, about 300 days or more, about 600 days or more, or about 1000 days or less. Thus, the level of bioerosion can be tailored to achieve a given level of mass reduction over a certain desired duration. For example, a medical device (e.g., a tissue scaffold) can reach about 75% reduction in mass in about 30 days. As another example, a tissue scaffold can have about 30% reduction in mass in about 180 days.

In some embodiments, the tissue scaffold includes each of filaments 22 and 24 at a concentration from about one weight percent to about 99 weight percent. Filament 22 and filament 24 concentrations can each independently be greater than or equal to about one weight percent, about two weight percent, about three weight percent, about five weight percent, about ten weight percent, about 20 weight percent, about 30 weight percent, about 40 weight percent, about 50 weight percent, about 60 weight percent, about 70 weight percent, about 80 weight percent, about 90 weight percent, or about 95 weight percent; and/or less than or equal to about 99 weight percent, about 98 percent, about 97 percent, about 95 percent, about 90 percent, about 80 percent, about 70 percent, about 60 percent, about 50 percent, about 40 percent, about 30 percent, about 20 percent, about 10 percent, about five percent, about three percent, or about two percent.

In some embodiments, filaments have a sub-micron (e.g., less than one micron) width or diameter and are nanofilaments. A tissue scaffold including one or more filaments (e.g., nanofilaments) having a sub-micron width or diameter can, for example, enhance the bioerodibility of the tissue scaffold by increasing the surface area available for bioerosion, and can provide an increased pore volume for better cell growth. In embodiments, each of the filaments 22 and 24 can have an average width or diameter from about five nm to about 500 nm. The average width or diameter of filament 22 and filament 24 can each independently be greater than or equal to about five nm, about 10 nm, about 25 nm, about 50 nm, about 75 nm, about 100 nm, about 125 nm, about 150 nm, about 175 nm, about 200 nm, about 225 nm, about 250 nm, about 300 nm, about 350 nm, about 400 nm, or about 450 nm; and/or less than or equal to about 500 nm, about 450 nm, about 400 nm, about 350 nm, about 300 nm, about 250 nm, about 225 nm, about 200 nm, about 175 nm, about 150 nm, about 125 nm, about 100 nm, about 75 nm, about 50 nm, about 25 nm, or about 10 nm. For example, each of the filaments 22 and 24 can have a width or diameter of from about 50 nm to about 300 nm.

The width or diameter of filaments 22 and/or 24 can be substantially uniform along a length of the filaments. A filament can have a width or diameter that varies from about ±1 percent to about ±25 percent of the average width or diameter value over a filament length. The filament width or diameter variation can be greater than or equal to about ±1 percent, about ±2 percent, about ±4 percent, about ±6 percent, about ±8 percent, about ±10 percent, about ±13 percent, about ±15 percent, about ±20 percent, or about ±22 percent; and/or less than or equal to about ±25 percent, about ±22 percent, about ±20 percent, about ±15 percent, about ±13 percent, about ±10 percent, about ±8 percent, about ±6 percent, about ±4 percent, or about ±2 percent of the average width or diameter value over the length of the filament. A substantially uniform width or diameter can provide a homogeneous environment for cell growth and/or can promote cell growth. The substantially uniform width or diameter of the filaments can allow the total surface area of the filament network to be calculated, given that the weight of the filaments and the density of the polymer material for a given filament width or diameter are known. As an example, for a filament of diameter d and length l, with a uniform perfectly cylindrical constant cross-section along its length, the surface area can be calculated from πdl, ignoring contributions from the ends of the filaments.

In some embodiments, a filament is not perfectly circular in cross-section (e.g., oval, elliptical, regularly polygonal, or irregularly polygonal in cross section). The average width or diameter of the filament having an irregular cross-section along a given length can refer to an average distance of any two orthogonal lines that both pass through the geometric center of the filament cross-section and have end points on the perimeter of the filament, or to the distance of any one such line.

In some embodiments, the filament width or diameter can affect the release (e.g., elution) of a biomolecule and/or therapeutic absorbed in the filament. For example, a filament having a relatively small width or diameter can have a relatively high biomolecule and/or therapeutic agent elution rate; a filament having a relatively large width or diameter can have a relatively low biomolecule and/or therapeutic agent elution rate.

In some embodiments, each of the filaments (e.g., nanofilaments) 22 and 24 has a length from about 10 μm to about 10 cm. Filament 22 and filament 24 widths or diameters can each be greater than or equal to about 10 μm, about 50 μm, about 100 μm, about 150 μm, about 500 μm, about 1 mm, about 5 mm, about 1 cm, about 2 cm, about 3 cm, about 4 cm, about 5 cm, about 7 cm, about 8 cm, or about 9 cm; and/or less than or equal to about 10 cm, about 9 cm, about 8 cm, about 7 cm, about 5 cm, about 4 cm, about 3 cm, about 2 cm, about 1 cm, about 5 mm, about 1 mm, about 500 μm, about 150 μm, about 100 μm, or about 50 μm. A tissue scaffold including one or more relatively long filaments can, for example, allow for better attachment of cells (e.g., nerve cells) and help orient the cells in a certain direction.

In some embodiments, filaments forming the tissue scaffold have a large length distribution, such that the tissue scaffold can have both short and long filaments. In some embodiments, filaments forming the tissue scaffold are generally uniform in length, for example, filaments can have a length that varies from about ±1 percent to about ±10 percent of the average filament length value. The filament length variation can be greater than or equal to about ±1 percent, about ±2 percent, about ±3 percent, about ±4 percent, about ±5 percent, about ±6 percent, about ±7 percent, about ±8 percent, or about ±9 percent; and/or less than or equal to about ±10 percent, about ±9 percent, about ±8 percent, about ±7 percent, about ±6 percent, about ±5 percent, about ±4 percent, about ±3 percent, or about ±2 percent of the average filament length value.

In some embodiments, each of the filaments 22 and 24 has a length-to-width or length-to-diameter aspect ratio of from about 100:1 to about 20,000, 000:1. The length-towidth or length-to-diameter aspect ratio for each of the filaments 22 and 24 can be greater than or equal to about 100:1, about 500:1, about 1,000:1, about 5,000:1, about 10,000:1, about 100,000:1, about 1,000, 000:1, or about 10,000, 000:1; and/or less than or equal to about 20,000, 000:1, about 10,000, 000:1, about 1,000, 000:1, about 100,000:1, about 10,000:1, about 5,000:1, about 1,000:1, or about 500:1. Different aspect ratios can enhance the growth of a variety of cell types. For example, a bone cell can be cultured on filaments with a relatively low aspect ratio, while a nerve can be cultured on filaments with a relatively large aspect ratio.

In some embodiments, at least one of the filaments 22 and 24 has a length greater than or equal to about 5 nm and less than 1000 nm, such that at least one of the filaments 22 and 24 is in the shape of a particle measuring less than one micron in both length and width or diameter (e.g., a nanoparticle). The nanoparticle can have the larger of either a length, or a width or a diameter, at a value greater than or equal to about 5 nm, about 10 nm, about 20 nm, about 50 nm, about 100 nm, about 200 nm, about 300 nm, about 400 nm, about 500 nm, about 600 nm, about 700 nm, about 800 nm, about 900 nm, or about 950 nm; and/or less than or equal to 1000 nm, about 950 nm, about 800 nm, about 700 nm, about 600 nm, about 500 nm, about 400 nm, about 300 nm, about 200 nm, about 100 nm, about 50 nm, about 20 nm, or about 10 nm. The nanoparticle can facilitate the growth of certain cells. In some embodiments, the nanoparticle can have enhanced conductivity and/or processability. In some embodiments, the nanoparticle carries one or more biomolecules and/or therapeutic agents, which can be eluted from the nanoparticle. Examples of conductive nanoparticles are described, for example, in Choi et al., Synthetic Metals, 141 (2004), 293-299; Ramanaviciene, A., Colloids and Surfaces B: Biointerfaces, 48 (2006), 159-166. In some embodiments, the nanoparticle can include a magnetic particle (e.g., magnetite $Fe_3O_4$). A magnetic nanoparticle can be heated using an AC magnetic field. The heated magnetic nanoparticle can break a filament in which it is incorporated. In some embodiments, the heated magnetic nanoparticle can increase the drug releasing capability of a drug-eluting filament. In some embodiments, a tissue scaffold including magnetic nanoparticles attracts magnetic capsules including therapeutic agents, which can be administered after implantation of the tissue scaffold. Use of magnetic particles is discussed further in U.S. Ser. No. 60/845,136, filed Sep. 15, 2006, and U.S. Ser. No. 60/844, 898, filed Sep. 15, 2006.

In some embodiments, the tissue scaffold includes one or more crossing (e.g., intersecting, interpenetrating, interconnected) filaments 22 and/or 24. For example, multiple filaments 22 and/or 24 can cross one another at one or more points (e.g., locations) along the length of any filament to form a two-dimensional or a three-dimensional network. Referring to FIG. 2A, in some embodiments, crossing filaments 22 and/or 24 are substantially aligned along a given direction. For example, the filaments can have the same general orientation with respect to one another over a length of from about 10 μm to about 1 cm. The length over which the filaments can be oriented can be greater than or equal to about 10 μm, about 50 μm, about 100 μm, about 500 μm, about 750 μm, about 1 mm, about 3 mm, about 5 mm, about 7 mm, about 9 mm; and/or less than or equal to about 1 cm, about 9 mm, about 7 mm, about 5 mm, about 3 mm, about 1 mm, about 750 μm, about 500 μm, about 100 μm, or about 50 μm. Referring to FIG. 2B, in certain embodiments, filaments are randomly oriented and can cross one another at numerous points to form a network.

A tissue scaffold in the form of a network can define one or more pores (e.g., openings, voids between filaments), which can allow nutrients, fluids, small molecules, and gases to diffuse through the scaffold. In some embodiments, the tissue scaffold includes biomolecules and/or therapeutic agents, and a porous structure can expose a substantial portion of the filaments for biomolecule and/or therapeutic agent elution. A porous network can allow for cell growth and migration within the scaffold, while permitting waste products to be removed. A porous network can reduce the likelihood that an undesired cell type enters the scaffold. Porous scaffolds are described, for example, in Zhuang, S., Nature Biotechnology, 21 (2003), 1171-1178. In some embodiments, one or more pores defined within the tissue scaffold have an average volume of from about 0.01 $\mu m^3$ to about 100 $\mu m^3$. The average volume of the one or more pores can be greater than or equal to about 0.01 $\mu m^3$, about 0.1 $\mu m^3$, about 1 $\mu m^3$, about 25 $\mu m^3$, about 50 $\mu m^3$, or about 90 $\mu m^3$; and/or less than or equal to about 100 $\mu m^3$, about 90 $\mu m^3$, about 50 $\mu m^3$, about 25 $\mu m^3$, about 1 $\mu m^3$, or about 0.1 $\mu m^3$. The one or more pores can also be expressed using an average diameter, such that one or more pores defined within the scaffold network can have an average diameter of from about five $\mu m$ to about 30 $\mu m$. The average diameter of the one or more pores can be greater than or equal to about five $\mu m$, about eight $\mu m$, about ten $\mu m$, about 12 $\mu m$, about 15 $\mu m$, about 18 $\mu m$, about 20 $\mu m$, about 23 $\mu m$, or about 25 $\mu m$; and/or less than or equal to about 30 $\mu m$, about 25 $\mu m$, about 23 $\mu m$, about 20 $\mu m$, about 18 $\mu m$, about 15 $\mu m$, about 12 $\mu m$, about ten $\mu m$, or about eight $\mu m$. For example, one or more pores defined within the tissue scaffold can have an average diameter from about 10 $\mu m$ to 20 $\mu m$.

A tissue scaffold can include a first region and a second region defining one or more second pores. The first and second regions can occupy different locations within a tissue scaffold. For example, the first region can be in an interior region of a tissue scaffold and the second region can be in an exterior region of the tissue scaffold. In some embodiments, the first region is in an exterior region of a tissue scaffold and the second region is in an interior region of a tissue scaffold. In a generally spherical or circular tissue scaffold having a radius r, for example, the interior region can extend from a center C to a radius of about r/3 (e.g., about r/2, about 2r/3, about 3r/5, about 4r/5), and the exterior region can extend from a radius of about r/3 (e.g., about r/2, about 2r/3, about 3r/5, about 4r/5) to a radius of about r. In some embodiments, the first region extends a first length portion of a tissue scaffold and a second region extends a second length portion of a tissue scaffold. In some embodiments, a tubular tissue scaffold has a first region spanning part or all of the tubular interior and a second region spanning all or part of the tubular exterior. In some embodiments, the average volume of the pores defined in the second region is different from (e.g., greater than) the average volume of the pores defined in the first region. For example, the average volume of the pores defined in the second region can be at least about 1,000 times greater than the average volume of the pores defined in the first region.

In some embodiments, a tissue scaffold includes a pore distribution such that the pore density (e.g., number of pores per volume) of the first region is different from the pore density of the second region of the tissue scaffold. In some embodiments, the pore density of the second region is at least about two times higher (e.g., about three times higher, about four times higher, about five times higher, about six times higher, about ten times higher) than the pore density of the first region.

In some embodiments, a tissue scaffold has a porosity (i.e., the percentage of void volume per total tissue scaffold volume) from about 10 percent by volume to about 95 percent by volume. The tissue scaffold porosity can be greater than or equal to about 10 percent by volume, about 20 percent by volume, about 30 percent by volume, about 40 percent by volume, about 50 percent by volume, about 60 percent by volume, about 70 percent by volume, about 80 percent by volume, or about 90 percent by volume; and/or less than or equal to about 95 percent by volume, about 90 percent by volume, about 80 percent by volume, about 70 percent by volume, about 60 percent by volume, about 50 percent by volume, about 40 percent by volume, about 30 percent by volume, or about 20 percent by volume. Porosity can be measured using a porosimeter (e.g., a Micromeritics Autopore III porosimeter, available from Micromeritics, Norcross, Ga.). Porosity measurements are described, for example, in Cooper et al., Biomaterials, 26 (2005), 1523-1532. A tissue scaffold having a relatively large porosity can enhance nutrient, fluid, small molecule, and gas diffusion through the scaffold. A tissue scaffold having a large porosity can also have increased free volume, which can increase tissue growth in the scaffold. Tissue scaffolds having large porosity values are described, for example, in Moore et al., Biomaterials, 27 (2006) 419-429. In certain embodiments, the first and/or second regions of the tissue scaffold do not define any pores.

The tissue scaffold can be made using the FFESS technique. In the FFESS technique, the polymer/solvent solution can be formed by dissolving one or more polymers such as a conducting polymer and one or more dopants, and/or a bioerodible polymer in one or more solvents. For example, conducting polymers such as polypyrroles and/or polythiophenes synthesized via chemical oxidation or electrodeposition, and bioerodible polymers such poly(D,L-lactide) and/or poly(D,L-lactide-co-glycolide), can be dissolved in a suitable solvents such as chloroform, ethanol, N-methyl-2-pyrrolidinone, N,N-dimethylformamide, dimethyl sulfoxide, ethyl acetate, methylene chloride, acetone, trifluoroethanol, tetrahydrofuran, toluene, and/or acetonitrile. Examples of suitable solvents are described, for example, in Jang et al., Synthetic Metals, 150 (2005), 127-131.

In some embodiments, one or more biomolecules and/or therapeutic agents are further dissolved in polymer/solvent solution to form, for example, a blend or a composite.

The polymer solution is sprayed from a capillary in the FFESS process. The FFESS method for electro-spraying can create a filament network in which the one or more filaments have a highly controlled fiber width or diameter. In particular, by controlling the voltage, flow-rate, concentration of polymer in the spray fluid, the viscosity of the spray fluid, and the distance of the nozzle from the surface of the underlying structure 10, the width or diameter of the filaments formed during the spinning process can be controlled. Environmental factors, such as temperature, pressure, solvent vapor pressure, can also determine the width or diameter of the filaments.

In some embodiments, the DC voltage difference between the nozzle and the collection substrate is from about 5 kV to about 50 kV. The DC voltage difference can be greater than or equal to about five kV, about ten kV, about 20 kV, about 30 kV, or about 40 kV and/or less than or equal to about 50 kV, about 40 kV, about 30 kV, about 20 kV, or about ten kV.

In some embodiments, the polymer flow rate is from about 0.0003 ml/min to about 0.01 ml/min. The polymer flow rate can be greater than about 0.0003 ml/min, about 0.001 ml/min, about 0.005 ml/min, or about 0.008 ml/min; and/or less than or equal to about 0.01 ml/min, about 0.008 ml/min, about 0.005 ml/min, or about 0.001 ml/min.

In some embodiments, a polymer/solvent solution has a total polymer concentration from about two mol percent to about 25 mol percent. The total polymer concentration can be greater than or equal to about two mol percent, about five mol percent, about ten mol percent, about 15 mol percent, or about 20 mol percent; and/or less than or equal to about 25 mol percent, about 20 mol percent, about 15 mol percent, about ten mol percent, or about five mol percent.

The polymer/solvent solution can have a viscosity from about 100 cps to about 10,000 cps. The polymer/solvent solution viscosity can be greater than or equal to about 100 cps, about 1,000 cps, about 2,000 cps, about 5,000 cps, about 7,500 cps, or about 9,000 cps; and/or less than or equal to about 10,000 cps, about 9,000 cps, about 7,500 cps, about 5,000 cps, about 2,000 cps, or about 1,000 cps.

In some embodiments, the distance between the nozzle and the collection substrate is from about three cm to about 30 cm. The distance between the nozzle and the collection substrate can be greater than or equal to about three cm, about seven cm, about ten cm, about 15 cm, about 20 cm, or about 25 cm; and/or less than or equal to about 30 cm, about 25 cm, about 20 cm, about 15 cm, about ten cm, or about seven cm. A large distance between the nozzle and the collection plate can provide a longer time duration for the sprayed filaments to dry before collection, which can result in separated filaments. A smaller distance between the nozzle and the collection plate can provide a shorter time duration for the filaments to dry before collection, which can result in fused filaments on the collection plate.

The polymer solution is sprayed from capillary onto a grounded collection substrate. For example, the polymer solution can be sprayed as a continuous jet, as an interrupted jet, or as droplets. As an example, as the polymer solution is drawn toward the collection substrate, the solvent can fully or partially vaporize to form a continuous polymer filament from a continuous polymer solution jet, a broken polymer filament from an interrupted polymer solution jet, or nanoparticles (e.g., particles, beads) from polymer solution droplets. In some embodiments, the collected polymer forms filament network sheets, or three dimensional porous structures. In some embodiments, different filaments including different polymers, biomolecules and/or therapeutic agents, are sprayed using multiple nozzles to achieve a mixture of different filaments on a collection substrate. As an example, a 60 nm diameter filament can be obtained by spraying a solution of polystyrene (molecular weight 212,000) in tetrahydrofuran at a field strength of 20 kV/20 cm. A 200 nm diameter filament can be obtained by spraying a solution of 350 mg polyaniline doped with 2-acrylamido-2-methyl-1-1propanesulfonic acid in 1.5 ml concentrated $H_2SO_4$ at a field strength of 30 kV/3 cm. A blended filament can be obtained by spraying a solution of 100 mg polyaniline doped with 129 mg of camphorsulfonic acid and 10 mg of polyethylene oxide (molecular weight 900,000) in 10 ml of chloroform at a field strength of 8 kV/30 cm. The filaments can be sprayed simultaneously from different nozzles, or in sequence from the same or different nozzles.

In some embodiments, the collection substrate is a rotating mandrel or a rotating disk. A filament can be sprayed and spooled onto the rotating mandrel or collected onto the rotating disk at a given speed. The mandrel or the disk can have a rotation speed that is relatively fast, which can afford a filament network having relatively large pores. In some embodiments, the rotation speed of the mandrel or the disk is relatively slow, which can afford a filament network having relatively small pores.

In some embodiments, the collection substrate includes a filament network at an amount from about ten percent to about 50 percent by weight of the substrate. The filament network can be greater than or equal to about ten percent by weight, about 15 percent by weight, about 20 percent by weight, about 25 percent by weight, about 30 percent by weight, about 35 percent by weight, about 40 percent by weight, or about 45 percent by weight; and/or less than or equal to about 50 percent by weight, about 45 percent by weight, about 40 percent by weight, about 35 percent by weight, about 30 percent by weight, about 25 percent by weight, about 20 percent by weight, or about 15 percent by weight of the substrate. For example, the filament network can be about 20% to about 30% by weight of the substrate.

In some embodiments, the filament network is stretched along a given direction (e.g., longitudinal, diagonal, or latitudinal) to orient the filaments, such that the filaments are aligned along the stretching direction. An aligned filament network can, for example, assist in orienting and directing cell growth along a certain direction.

In some embodiments, the tissue scaffold includes (e.g., is formed of) a filament network that is self-supporting and/or can retain structural integrity without the presence of a substrate. For example, the filament network can maintain an original shape or a close approximation thereof after removal or disappearance (e.g., bioerosion) of a supporting substrate. A tissue scaffold including (e.g., formed of) a self-supporting filament network can bioerode relatively quickly, can be relatively more biocompatible and/or can enhance tissue growth.

In some embodiments, the tissue scaffold includes a bioerodible filament network and a bioerodible substrate that supports the filament network. The filament network can bioerode in a controllable manner and tune the bioerosion of the substrate.

In some embodiments, the collection substrate includes (e.g., is formed of) a bioerodible material, such as a bioerodible metal, a bioerodible metal alloy, or a bioerodible nonmetal or a non-bioerodible material. The substrate may be used as a component of the scaffold or the substrate may be removed from the deposited material, which is used as a scaffold. Bioerodible materials are described, for example, in U.S. Pat. No. 6,287,332 to Bolz; U.S. Patent Application Publication No. US 2002/0004060 A1 to Heublein; U.S. Pat. Nos. 5,587,507 and 6,475,477 to Kohn et al. Examples of bioerodible metals for use with the underlying structure include alkali metals, alkaline earth metals (e.g., magnesium), iron, and zinc. Examples of biodisintegrable metal alloys include alkali metal alloys, alkaline earth metal alloys (e.g., magnesium alloys), iron alloys (e.g., alloys including iron and up to seven percent carbon), zinc alloys, and aluminum alloys.

In some embodiments, a bioerodible material from which the collection substrate is formed includes at least one metallic component and at least one non-metallic component, or at least two different metallic components. In some embodiments, a bioerodible metal includes at least one of the following: manganese, cobalt, nickel, chromium, copper, cadmium, lead, tin, thorium, zirconium, silver, gold, palladium, platinum, rhenium, silicon, calcium, lithium, aluminum, zinc, iron, carbon, and sulfur. In certain embodiments, an erodible material includes at least two of the following metals in proportions by weight of greater than about 1%: magnesium, titanium, zirconium, niobium, tantalum, zinc, or silicon, and lithium, sodium, potassium, calcium, iron, or manganese. In certain embodiments, the bioerodible material includes a first component selected from the group consisting of: magnesium, titanium, zirconium, niobium, tantalum, zinc, silicon, and another, different, component selected from the group consisting of: lithium, sodium, potassium, calcium, iron, manganese.

Examples of bioerodible non-metals include bioerodible polymer, such as polyiminocarbonates, polycarbonates, polyarylates, polylactides, or polyglycolic esters. In some embodiments, a bioerodible metal and/or a metal alloy is sintered. In some embodiments, the bioerodible material is a polymer, such as, without limitation, those described at cols. 8-9 of U.S. Pat. No. 6,918,869 to Shaw et al.

In some embodiments, the bioerodible collection substrate material can be a ceramic such as an alumina-based ceramic, or a glass-based ceramic such as Macor® (55% mica crystal, 45% matrix glass, available from Corning Incorporated).

In some embodiments, a tissue scaffold made by FFESS is used to grow cells. For example, cells can be isolated from a subject, cultured in vitro in a suitable medium for a desired duration (e.g., 8 hours, 24 hours, or 72 hours), and/or seeded onto a tissue scaffold by allowing the cells to adhere to the scaffold in a humidified incubator for a desired duration (e.g., 8 hours, 24 hours, or 72 hours). Methods of seeding a substrate with cells are described, for example, in Lakard et al., Biosensors and Bioelectronics, 20 (2005), 1946-1954; Schmidt, Annu Rev. Biomed. Eng. 5 (2003), 293-347; and Zhang et al., Seminars in Cancer Biology, 15 (2005), 413-420. The cell-seeded tissue scaffold can be incubated and electrically stimulated in vitro for a period of time and implanted into the subject or a different subject. As an example, the subject can be a mouse, a pig, a sheep, or a human. In some embodiments, the tissue scaffold is seeded with a particular cell type and directly implanted into a subject. In other embodiments, the tissue scaffold is directly implanted into a subject without cell seeding. Implantation of tissue scaffolds is described, for example, in Schmidt, Annu Rev. Biomed. Eng. 5 (2003), 293-347.

The tissue scaffold can be electrically stimulated within a subject, e.g., using an implanted battery power source. In some embodiments, the applied electrical stimulus is from about 1 mA to about 10 mA. The electrical stimulus can be greater than or equal to about one mA (e.g., about five mA, or about eight mA); and/or less than or equal to about ten mA (e.g., about eight mA, or about five mA) at a coulomb dosage of at least about 1 C/cm$^2$ (e.g., from about 5 C/cm$^2$, from about 1° C./cm$^2$, from about 2° C./cm$^2$) and/or at most about 25 C/cm$^2$ (e.g., at most about 2° C./cm$^2$, at most 10 C/cm$^2$, at most 5 C/cm$^2$). Suitable current and dosage ranges are described, for example, in Nilsson et al., Bioelectrochemistry, 53 (2001), 213-224. The tissue scaffold can bioerode over a period of time during which the seeded cells can propagate and form a new tissue. A variety of cells can be grown on the tissue scaffold, such as muscle cells, endothelial cells, nerve cells, neurons, bones, cardiac myocytes, cardiac cells, and/or blood vessel cells. In some embodiments, a tissue scaffold is not electrically stimulated for cell colonization and growth.

Further examples of tissues are described, for example, in http://reach.ucf.edu/~OncEduc1/. Depending on the desired tissue, the tissue scaffold can be in the form of, for example, a porous generally spherical or cylindrical structure (e.g., for a neural prosthetic, or a nerve conduit), a porous generally planar structure (e.g., for a heart valve), a porous generally tubular or branched tubular structure (e.g., for a blood vessel), or a porous film structure (e.g., for a skin scaffold). The tissue scaffold can also be implanted at various body locations such as in a brain; at a ligament, nerve, muscle or eye; or near damaged blood vessels.

While a number of embodiments have been described above, the invention is not so limited.

In some embodiments, a tissue scaffold includes nanofilaments on a network of filaments having larger diameters and/or lengths of the same or different material as the nanofilaments. The larger filaments can reinforce the tissue scaffold structure, while the nanofilaments can serve as a growth environment for tissues. The nanofilaments and the larger filaments can be present at a ratio of, for example, 100:1, 1,000:1, 10,000:1.

As an example, the filament network of the tissue scaffold can contain a nanocomposite instead of or in addition to a purely polymeric material. "Nanocomposite" refers to a composition comprising a polymeric material and relatively small amounts (generally less than about 10% by weight) of nanometer-sized (average size smaller than 1 micrometer) mineral, clay, or nanosized ceramic particles dispersed therein. Sometimes nanocomposites are referred to as "nanoclay" or "nanoceramic". For example, nanocomposites are disclosed in International Publication No. WO 93/1014118, and U.S. Pat. Nos. 5,385,776, and 6,251,980, all of which are incorporated herein by reference in their entirety. These particles may themselves contain therapeutic agents that are released as the polymer of the network degrades.

As an example, while the tissue scaffold is shown as including one or more biomolecules and/or therapeutic agents in the form of a composite or a blend within a filament or a nanoparticle, in some embodiments, the biomolecules and/or therapeutic agents are encapsulated in a liposome and embedded in a tissue scaffold. Liposomes are lipid-bilayer bound vesicles, typically less than 1 micron in diameter, for example, in the range 50 nm-400 nm in diameter, that can be used as drug-delivery vehicles. The encapsulated biomolecules and/or therapeutic agents can elute from the liposomes in a subject. Liposome-encapsulated biomolecules and/or therapeutic agents can be dissolved in a polymer solution prior to FFESS and incorporated into the sprayed filament or nanoparticle. In some embodiments, liposome-encapsulated biomolecules and/or therapeutic agents can be sprayed onto the tissue scaffold using a secondary nozzle.

In some embodiments, one or more biomolecules and/or a therapeutic agents are coated onto a tissue scaffold. For example, a biomolecule and/or a therapeutic agent can be dissolved in a solvent and sprayed onto a tissue scaffold. As an example, a tissue scaffold can be dipped into a solution containing a biomolecule and/or a therapeutic agent. The biomolecule and/or therapeutic agent can be bound to the tissue scaffold by non-covalent interactions such as hydrogen bonding, electrostatic, van der Waals, and/or hydrophobic/lipophilic interactions. In some embodiments, a tissue scaffold is chemically reacted with a biomolecule and/or a therapeutic agent. The biomolecule and/or therapeutic agent can be covalently bound to the tissue scaffold.

In certain embodiments, different regions of the tissue scaffold are coated with different numbers of layers including one or more biomolecules and/or therapeutic agents. In some embodiments, one region of the tissue scaffold bioerodes at a faster rate than another region of the tissue scaffold. The coating layers can control the bioerosion rate at different region of the tissue scaffold. In some embodiments, a tissue scaffold includes an arrangement of coating layers that causes one or more regions of the tissue scaffold to start bioeroding before the remaining regions of the tissue scaffold. This can limit the likelihood of the tissue scaffold of breaking into two or more pieces during bioerosion.

In some embodiments, a tissue scaffold further includes one or more biomolecules and/or therapeutic agents, such as chemical compounds, growth factors, enzymes, peptides, polysaccharides, and/or oligonucleotides. Examples of biomolecules include small molecules (e.g., lipids, phospholipids, glycolipids, sterols, vitamins, hormones, neurotransmitters, carbohydrates, sugars, disaccharides), monomers (e.g., amino acids, nucleotides, nucleic acids, phosphates, monosaccharides), polymers (e.g., peptides, oligopeptides, polypeptides, proteins, DNA, RNA, oligosaccharides, polysaccharides), and/or macromolecules (e.g., prions). The biomolecule and/or therapeutic agent can control and/or direct cell growth on a tissue scaffold, and/or can allow the growth of a tissue with characteristics (e.g., orientation, differentiation, functionality) that can be beneficial to a subject.

"Biologically active agents," "drugs," "therapeutic agents," "pharmaceutically active agents," "pharmaceutically active materials," and other related terms may be used interchangeably herein and include genetic therapeutic agents, non-genetic therapeutic agents and cells. A wide variety of therapeutic agents can be employed in conjunction with the present invention. Numerous therapeutic agents are described here. For example, a tissue scaffold can include non-genetic therapeutic agents such as: a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, antimicrobial peptides such as magainins, aminoglycosides and nitrofurantoin; (m) cytotoxic agents, cytostatic agents and cell proliferation affectors; (n) vasodilating agents; (O) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin; (t) beta-blockers; (u) bARKct inhibitors; (v) phospholamban inhibitors; (w) Serca 2 gene/protein; (x) immune response modifiers including aminoquizolines, for instance, imidazoquinolines such as resiquimod and imiquimod; and (y) human apolioproteins (e.g., AI, AII, AIII, AIV, AV, etc.).

The tissue scaffold can include other non-genetic therapeutic agents such as paclitaxel (including particulate forms thereof, for instance, protein-bound paclitaxel particles such as albumin-bound paclitaxel nanoparticles, e.g., ABRAXANE), sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well as derivatives of the foregoing, among others.

Exemplary genetic therapeutic agents for use in connection with the tissue scaffold include anti-sense DNA and RNA as well as DNA coding for: (a) anti-sense RNA; (b) tRNA or rRNA to replace defective or deficient endogenous molecules; (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor; (d) cell cycle inhibitors including CD inhibitors; and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in connection with the tissue scaffold include cells of human origin (autologous or allogeneic), including whole bone marrow, bone marrow derived mono-nuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and suitable examples may be selected from one or more of the following: (a) Ca-channel blockers including benzothiazapines such as diltiazem and clentiazem, dihydropyridines such as nifedipine, amlodipine and nicardapine, and phenylalkylamines such as verapamil; (b) serotonin pathway modulators including: 5-HT antagonists such as ketanserin and naftidrofuryl, as well as 5-HT uptake inhibitors such as fluoxetine; (c) cyclic nucleotide pathway agents including phosphodiesterase inhibitors such as cilostazole and dipyridamole, adenylate/Guanylate cyclase stimulants such as forskolin, as well as adenosine analogs; (d) catecholamine modulators including α-antagonists such as prazosin and bunazosine, β-antagonists such as propranolol and α/β-antagonists such as labetalol and carvedilol; (e) endothelin receptor antagonists; (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., 5-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine; (g) Angiotensin Converting Enzyme (ACE) inhibitors such as cilazapril, fosinopril and enalapril; (h) ATII-receptor antagonists such as saralasin and losartin; (i) platelet adhesion inhibitors such as albumin and polyethylene oxide; (j) platelet aggregation inhibitors including cilostazole, aspirin and thienopyridine (ticlopidine, clopidogrel) and GP IIb/IIIa inhibitors such as abciximab, epitifibatide and tirofiban; (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C; (l) cyclooxygenase pathway inhibitors such as aspirin, ibuprofen, flurbiprofen, indomethacin and sulfinpyrazone; (m) natural and synthetic corticosteroids such as dexamethasone, prednisolone, methprednisolone and hydrocortisone; (n) lipoxygenase pathway inhibitors such as nordihydroguairetic acid and caffeic acid; (O) leukotriene receptor antagonists; (p) antagonists of E- and P-selectins; (q) inhibitors of VCAM-1 and ICAM-1 interactions; (r) prostaglandins and analogs thereof including prostaglandins such as PGE1 and PGI2 and prostacyclin analogs such as ciprostene, epoprostenol, carbacyclin, iloprost and beraprost; (s) macrophage activation preventers including bisphosphonates; (t) HMG-CoA reductase inhibitors such as lovastatin, pravastatin, fluvastatin, simvastatin and cerivastatin; (u) fish oils and omega-3-fatty acids; (v) free-radical scavengers/antioxidants such as probucol, vitamins C and E, ebselen, trans-retinoic acid and SOD mimics; (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives; (x) MMP pathway inhibitors such as marimastat, ilomastat and metastat; (y) cell motility inhibitors such as cytochalasin B; (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin; (aa) matrix deposition/organization pathway inhibitors such as halofuginone or other quinazolinone derivatives and tranilast; (bb) endothelialization facilitators such as VEGF and RGD peptide; and (cc) blood rheology modulators such as pentoxifylline.

The one or more biomolecules and/or therapeutic agents can be incorporated into the tissue scaffold by a variety of processes. For example, the one or more biomolecules and/or therapeutic agents can be adsorbed or absorbed onto the filaments and/or nanoparticles forming the tissue scaffold. The one or more biomolecules and/or therapeutic agents can be covalently linked to the conducting polymer and/or the bioerodible polymer in the filaments and/or nanoparticles. The one or more biomolecules and/or therapeutic agents can be electrostatically associated with the conducting polymer and/or the bioerodible polymer in filaments 22 and/or 24. The one or more biomolecules and/or therapeutic agents can form a blend or a composite with the conducting polymer and/or the bioerodible polymer. In some embodiments, the one or more biomolecules and/or therapeutic agents are uniformly dispersed within part or all of the tissue scaffold. In some embodiments, the one or more biomolecules and/or therapeutic agents are non-uniformly dispersed within part or all of the tissue scaffold (e.g., in an increasing or decreasing gradient from a first region to a second region, in a stepwise manner of increase or decrease from a first region to a second region). In some embodiments, using FFESS, a thinner filament network can be formed at the end sections of a tissue scaffold, and a higher biomolecule and/or therapeutic agent elution at the ends can be obtained due to an increased surface area to volume ratio of the filaments. In some embodiments, the one or more therapeutic agents can have elution rates that are tailored for a desired cell type.

The tissue scaffold can have a biomolecule and/or therapeutic agent amount of from about one weight percent to about 50 weight percent. The biomolecule and/or therapeutic agent amount in the tissue scaffold can be greater than or equal to about one weight percent, about five weight percent, about ten weight percent, about 20 weight percent, about 30 weight percent, about 40 weight percent, or about 45 weight percent; and/or less than or equal to about 50 weight percent, about 45 weight percent, about 40 weight percent, about 30 weight percent, about 20 weight percent, about ten weight percent, or about five weight percent.

The one or more biomolecules and/or therapeutic agents can be released from the tissue scaffold at a given elution rate. For example, the one or more biomolecules and/or therapeutic agents can be released at a constant elution rate from the tissue scaffold over a time period. In some embodiments, the one or more biomolecules and/or therapeutic agents are released at an increasing or at a decreasing elution rate from the tissue scaffold over a time period. In some embodiment, elution occurs sequentially depending on the biomolecule and/or therapeutic agent. For example, one type of a biomolecule (e.g., a first growth factor) can elute before a second type of a biomolecule (e.g., a second growth factor). The different elution rates can provide growth environments for different types of cells and/or can assist in the formation of complex organs such as blood vessels.

Examples of therapeutic agents can be found at cols. 4-6 of U.S. Pat. No. 6,899,731 to Li et al., and at cols. 5-8 of U.S. Pat. No. 6,923,996 to Epstein et al., the disclosures of which are incorporated by reference in their entirety. It is to be understood that the therapeutic agents that can be used are not limited to those found herein.

Examples of therapeutic agents and methods of incorporating such agents into a multi-layer structure are described in U.S. patent application Ser. No. 10/849,742, filed May 20, 2004. U.S. Pat. No. 5,733,925, to Kunz et al., also provides general guidance for incorporating therapeutic agents into layers.

The filament network or a tissue scaffold can instead or additionally be used to deliver an antimicrobial agent, such as for the purpose of preventing or limiting local infection in the vicinity of the device. Exemplary antimicrobial agents have broad-spectrum activity and include triclosan, chlorhexidine, silver sulfadiazine, silver ions, benzalkonium chloride, and zinc pyrithione, as well as broad-spectrum antibiotics such as quinolones, fluoroquinolones, aminoglycosides and sulfonamides. Antiseptics such as iodine, methenamine, nitrofurantoin, validixic acid and other acidifying agents, including acids extracted from cranberry juice may also be used.

In some embodiments, the medical device is a cardiac tissue scaffold, a neural tissue scaffold, a neuro-vascular network, and/or a neural implant.

In some embodiments, the medical device is an implantable bioelectric circuit having an anode and a cathode including (e.g., formed of) electrically conducting polymers. The implantable bioelectric circuit can include one or more ionically conducting polymers and electrolytes. The implantable bioelectrical circuit can be electrically conducting and can be a component, for example, of a neural network. Another technique for forming filaments is electrospinning Electrospinning is described, for example, in Zong et al., Biomaterials, 26 (2005), 5330-5338 and Chronakis et al., Polymer, 47 (2006), 1597-1603.

All non-patent literature publications, patent applications, patent application publications, and patents, referred to in the instant application are incorporated herein by reference in their entirety.

Other embodiments are to be found within the appended claims.

What is claimed is:

1. A tissue scaffold, comprising:
a plurality of polymeric filaments having a diameter of about 5 to 500 nm, the filaments comprising a conducting polymer comprising an anionic dopant, and the filaments comprising a first filament having a first conducting polymer and a second filament having a second conducting polymer, and the second conducting polymer being different from the first conducting polymer, and
the tissue scaffold being at least partially erodible and defining pores having a diameter from 5 μm to 25 μm between the filaments.

2. The tissue scaffold of claim 1, wherein the conducting polymer is bioerodible.

3. The tissue scaffold of claim 1, wherein the conducting polymer is non-erodible.

4. The tissue scaffold of claim 1, wherein the filaments include a combination of polymers, including a conducting polymer and a non-conducting polymer.

5. The tissue scaffold of claim 4, wherein the non-conducting polymer is erodible.

6. The tissue scaffold of claim 4, wherein the non-conducting polymer is non-erodible.

7. The tissue scaffold of claim 1, wherein the scaffold includes a first filament including a conducting polymer and a second filament including a non-conducting polymer.

8. The tissue scaffold of claim 1, wherein the filaments have a substantially uniform diameter along a length.

9. The tissue scaffold of claim 1, wherein the filaments have a length-to-diameter aspect ratio of from 100:1 to 10,000:1.

10. The tissue scaffold of claim 1, wherein the conducting polymer has a conductivity of from $0.1\ \text{Scm}^{-1}$ to $50\ \text{Scm}^{-1}$.

11. The tissue scaffold of claim 1, wherein the conducting polymer comprises a polymer selected from the group consisting of polypyrrole, polythiophene, polyaniline, substituted polypyrrole, substituted polythiophene, substituted polyaniline, and combinations thereof.

12. The tissue scaffold of claim 11, wherein the substituted polypyrrole, substituted polythiophene, and substituted polyaniline comprise a side chain including an ionizable and hydrolyzable moiety.

13. The tissue scaffold of claim 1, wherein the second conducting polymer comprises a polymer selected from the group consisting of polypyrrole, polythiophene, polyaniline, substituted polypyrrole, substituted polythiophene, substituted polyaniline, and combinations thereof.

14. The tissue scaffold of claim 4, wherein the non-conducting polymer comprises a polymer selected from the group consisting of poly(D,L-lactide), poly(D,L-lactide-co-glycolide), polyanhydride, and combinations thereof.

15. The tissue scaffold of claim 1, wherein the second filament comprises a composite.

16. The tissue scaffold of claim 1, wherein the scaffold is selected from the group consisting of a vascular tissue scaffold, a cardiac tissue scaffold, a neural tissue scaffold, a bioelectric circuit, a neuro-vascular network, and a neural implant.

* * * * *